United States Patent
Dehghan Marvast et al.

(10) Patent No.: US 10,733,265 B2
(45) Date of Patent: *Aug. 4, 2020

(54) MEDICAL IMAGE MANAGER WITH AUTOMATED SYNTHETIC IMAGE GENERATOR

(71) Applicant: INTERNATIONAL BUSINESS MACHINES CORPORATION, Armonk, NY (US)

(72) Inventors: Ehsan Dehghan Marvast, Palo Alto, CA (US); Tanveer F. Syeda-Mahmood, Cupertino, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/412,628

(22) Filed: May 15, 2019

(65) Prior Publication Data
US 2019/0267131 A1 Aug. 29, 2019

Related U.S. Application Data

(63) Continuation of application No. 15/804,004, filed on Nov. 6, 2017.

(51) Int. Cl.
*G16H 30/20* (2018.01)
*G16H 15/00* (2018.01)
(Continued)

(52) U.S. Cl.
CPC ............ *G06F 19/321* (2013.01); *A61B 6/504* (2013.01); *A61B 6/5217* (2013.01);
(Continued)

(58) Field of Classification Search
None
See application file for complete search history.

(56) References Cited

U.S. PATENT DOCUMENTS 6,674,879 B1   1/2004 Weisman
6,983,063 B1   1/2006 Novak et al.
(Continued)

FOREIGN PATENT DOCUMENTS

DE      102006025761 A1    12/2007

OTHER PUBLICATIONS

IBM, List of IBM Patents or Patent Applications Treated as Related, Appendix P, dated Jun. 13, 2019, 2 pages.

*Primary Examiner* — David F Dunphy
(74) *Attorney, Agent, or Firm* — Tihon Poltavets (57) ABSTRACT

A method for processing medical images includes analyzing a medical image to detect a medical condition from a list of medical conditions, wherein the list of medical conditions includes aortic dissection, pulmonary embolism, and coronary stenosis. Responsive to determining the medical image includes a first medical condition, the method generates a first report that includes information on a detection of the first medical condition. The method identifies, a medical specialist based on availability and medical expertise and sends to the identified medical specialist, the medical image and the first report for a decision on the detection of the first medical condition. Responsive to receiving the decision from the medical specialist, the method sends to a second electronic device, the decision, the medical image, and the first report.

4 Claims, 6 Drawing Sheets

(51) Int. Cl.
  *A61B 6/00* (2006.01)
  *G06T 11/60* (2006.01)
  *G06T 7/00* (2017.01)
  *G06F 19/00* (2018.01)
  *G06T 7/62* (2017.01)
  *G16H 50/50* (2018.01)
  *G16H 50/20* (2018.01)
  *A61B 6/03* (2006.01)

(52) U.S. Cl.
  CPC ............ *A61B 6/5223* (2013.01); *A61B 6/563* (2013.01); *G06T 7/0012* (2013.01); *G06T 11/60* (2013.01); *G16H 15/00* (2018.01); *G16H 30/20* (2018.01); *A61B 6/032* (2013.01); *G06T 7/62* (2017.01); *G06T 2207/30104* (2013.01); *G06T 2210/41* (2013.01); *G16H 50/20* (2018.01); *G16H 50/50* (2018.01)

(56) References Cited

U.S. PATENT DOCUMENTS

| | | |
|---|---|---|
| 7,912,528 B2 | 3/2011 | Krishnan |
| 8,253,779 B2 | 8/2012 | Stetten |
| 8,515,778 B2 * | 8/2013 | Backhaus ............. G06F 19/321 705/2 |
| 9,467,789 B1 | 10/2016 | Zhao |
| 2003/0093294 A1 | 5/2003 | Passantino |
| 2005/0110791 A1 * | 5/2005 | Krishnamoorthy ....... G06T 7/60 345/419 |
| 2005/0240882 A1 * | 10/2005 | Morita ................... G06K 9/033 715/764 |
| 2006/0007188 A1 | 1/2006 | Reiner |
| 2006/0052690 A1 | 3/2006 | Sirohey |
| 2006/0215894 A1 | 9/2006 | Lakare |
| 2007/0248261 A1 * | 10/2007 | Zhou ..................... G06F 19/321 382/154 |
| 2008/0205589 A1 | 8/2008 | Camus |
| 2008/0317310 A1 | 12/2008 | Suresh |
| 2009/0003511 A1 * | 1/2009 | Roy .................... A61B 5/02007 378/4 |
| 2010/0119131 A1 | 5/2010 | Gebow |
| 2013/0039552 A1 | 2/2013 | Becker |
| 2014/0278462 A1 | 9/2014 | Jones et al. |
| 2015/0005630 A1 | 1/2015 | Jung |
| 2015/0206022 A1 | 7/2015 | Radha Krishna Rao |
| 2016/0321414 A1 * | 11/2016 | Salganicoff ............. G06F 19/00 |
| 2016/0364862 A1 | 12/2016 | Reicher |
| 2017/0018007 A1 | 1/2017 | Defrank |
| 2018/0108442 A1 | 4/2018 | Börve |
| 2018/0322254 A1 | 11/2018 | Smurro |
| 2019/0019286 A1 * | 1/2019 | Passerini ............... A61B 5/0035 |
| 2019/0027292 A1 | 1/2019 | Findeisen |
| 2019/0138689 A1 | 5/2019 | Dehghan Marvast et al. |
| 2019/0188848 A1 | 6/2019 | Madani |
| 2019/0188852 A1 | 6/2019 | Reicher |

* cited by examiner

MEDICAL IMAGE MANAGER WITH AUTOMATED SYNTHETIC IMAGE GENERATOR

FIELD OF INVENTION

This disclosure relates generally to medical images, and in particular to managing medical images with analysis and synthetic image generation.

BACKGROUND OF THE INVENTION

Typically, medical imaging is necessary for patients entering an emergency department with an unidentified condition. Timely diagnosis is key to allowing patients to receive accelerated and directed treatment prior to the condition worsening. Currently, the typical workflow for diagnosis includes an emergency department physician ordering an image study and a radiology technologist acquiring the required images, which are recorded in a Picture Archiving and Communication System (PACS). The image study is evaluated by a medical specialist, most commonly a radiologist, and the results are communicated back to the emergency department physician. A primary goal of the image study is to identify or rule out an abnormality (e.g., hemorrhage or dissection of the aorta) that is the cause for the unidentified condition. An availability of the medical specialist, a position of the imaging study in a priority list, and time required to review the image study, affect the timeliness for diagnosis of the unidentified condition.

SUMMARY

Embodiments in accordance with the present invention disclose a method, computer program product and computer system for processing medical images. Embodiments in accordance with the present invention analyze a medical image to detect a medical condition from a list of medical conditions, wherein the list of medical conditions includes aortic dissection, pulmonary embolism, and coronary stenosis. Embodiments in accordance with the present invention determine the medical image includes a first medical condition and generate a first report that includes information on a detection of the first medical condition. Embodiments in accordance with the present invention identify a medical specialist based on availability and expertise and send to a first electronic device associated with the identified medical specialist, the medical image and the first report for a decision on the detection of the first medical condition. Embodiments in accordance with the present invention receive the decision from the medical specialist and send to a second electronic device, the decision, the medical image, and the first report.

DETAILED DESCRIPTION

Embodiments of the present invention are directed to an image processing program capable of analyzing medical images (i.e., imaging study) to detect major abnormalities related to unidentified conditions of a patient in an emergency department. The image processing program is capable of processing large quantities of data in the form of numerous medical images for a patient, analyzing a medical image, determining whether a major abnormality exist in the medical image, generating a report and synthetic image based on the medical image, and prioritizing each medical image for a final decision by a medical specialist. By processing and analyzing medical images (e.g., Computed Topography Scan) for major abnormalities, such as aortic dissection, pulmonary embolism, and coronary stenosis, the image processing program can rule-in or rule-out major abnormalities as a diagnosis for an unidentified condition of a patient admitted into an emergency department. Ruling-in or ruling-out of major abnormalities is the determination of whether a major abnormality exists in the medical image and as a result, reduces the amount of time a medical specialist spends parsing through the medical images associated with a patient to determine a diagnosis.

The image processing program can generate a report that includes information pertaining to the ruling-in or ruling-out of major abnormalities that details how the image processing program arrived at a decision based on the analysis of the medical image. The generated report and the medical image are prioritized and sent to an identified medical specialist depending on an urgency of a decision from the medical specialist. Additionally, the image processing program can generate a synthetic image based on the medical image that assists the medical specialist in deciding whether to confirm or deny the ruling-in or ruling-out of major abnormalities. The computer generated synthetic image alters items in a medical image surrounding a major abnormality, to assist the medical specialist in focusing on an area where the major abnormality was detected.

Figure 1:
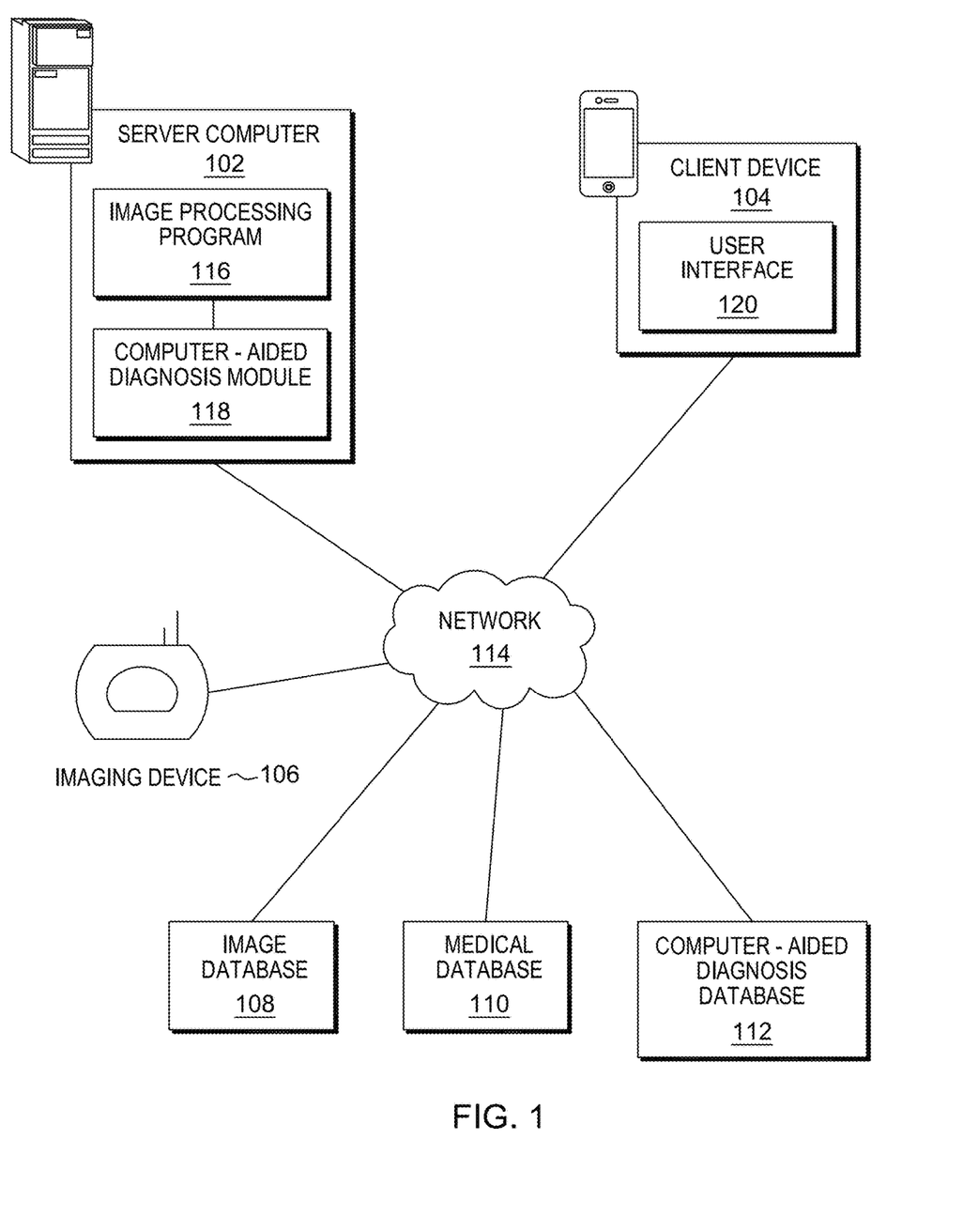
FIG. 1 is a functional block diagram illustrating a distributed data processing environment, in accordance with an embodiment of the present invention.

FIG. 1 is a functional block diagram illustrating a distributed data processing environment, in accordance with one embodiment of the present invention. The distributed data processing environment includes server computer 102, client device 104, imaging device 106, image database 108, medical database 110, and computer-aided diagnosis 112 all interconnected over network 114.

Server computer 102 may be a desktop computer, a laptop computer, a tablet computer, a specialized computer server, a smartphone, or any other computer system known in the art. In certain embodiments, server computer 102 represents a computer system utilizing clustered computers and components that act as a single pool of seamless resources when accessed through network 114, as is common in data centers and with cloud computing applications. In general, server computer 102 is representative of any programmable electronic device or combination of programmable electronic devices capable of executing machine-readable program instructions and communicating with other computer devices via a network. In this embodiment, server computer 102 has the ability to communicate with other computer devices to query the computer devices for information. Server computer 102 includes image processing program 116 and computer-aided diagnosis (CADx) module 118

Client device 104 may be a laptop computer, tablet computer, netbook computer, personal computer (PC), personal digital assistant (PDA), smart phone, wearable device (e.g., smart watch, personal fitness device, personal safety device), or any programmable computer system known in the art with an interactive display. Client device 104 includes user interface 120 and may include a client side image processing program 116, not illustrated in FIG. 1. In general, client device 104 is representative of any programmable electronic device or combination of programmable electronic devices capable of executing machine-readable program instructions and communicating with users of other electronic devices via network 114. Client device 104 may include components, as depicted and described in further detail with respect to FIG. 7, in accordance with embodiments of the present invention.

Imaging device 106 may be any medical device capable of producing a medical image such as, a computerized tomography (CT) scan which includes a large amount of data comprising a large quantity of images (i.e., slice). Medical images produced by imaging device 106 are stored in image database 108, where each medical image can include associated information such as, but not limited to, patient name, patient identification number, medical department identification, emergency department physician name, emergency department physician identification number, location, time, and date. Image database 108 can also store synthetic images that image processing program 116 generates by associating each synthetic image with a previously stored medical image. Medical database 110 stores medical information such as, but not limited to, medical specialist information, patient information, emergency department physician information, and patient medical records. Computer-aided diagnosis (CADx) database 112 stores algorithms for detecting medical conditions such as, but not limited to, aortic dissection, pulmonary embolism, and coronary stenosis. CADx database 112 also stores algorithms for generating synthetic images for medical conditions identified above.

Image processing program 116 can manage medical images by receiving a medical image from an image database 108. Image processing program 116 can analyze the received medical image for medical conditions that include aortic dissection, pulmonary embolism, and coronary stenosis based on algorithms stored in CADx database 112. Responsive to image processing program 116 not detecting a medical condition, image processing program 116 can generate a report providing information explaining why a medical condition was not detected in the received medical image. Image processing program 116 can queue the received image and the generated report, until image processing program 116 determines to send the received image and the generated report to a medical specialist to confirm the lack of a medical condition detection. Responsive to receiving a decision from the medical specialist, image processing program 116 sends the decision from the medical specialist to an emergency department physician associated with the received medical image.

Responsive to image processing program 116 detecting a medical condition (i.e., aortic dissection, pulmonary embolism, or coronary stenosis), image processing program 116 can generate a synthetic image of the detected condition in the received image. Image processing program 116 can generate a report providing information explaining why the medical condition was detected in the received medical image. Image processing program 116 can identify a medical specialist based on criteria (e.g., expertise or availability) and send the generated report, and the synthetic image of the detected condition to the identified medical specialist. Response to receiving a decision from the medical specialist, image processing program 116 sends the decision from the medical specialist to an emergency department physician associated with the received medical image. Computer-aided diagnosis (CADx) module 118 has the ability to perform a portion of the above mentioned steps including but not limited to detecting a medical condition (i.e., aortic dissection, pulmonary embolism, or coronary stenosis) and generating a synthetic image of the detected condition in the received image. CADx module 118 includes algorithms to analyze medical images for prominent abnormalities and generate synthetic images showing the abnormality upon detection.

In general, network 114 can be any combination of connections and protocols that will support communications between server computer 102 and client device 104. Network 114 can include, for example, a local area network (LAN), a wide area network (WAN), such as the internet, a cellular network, or any combination of the preceding, and can further include wired, wireless, and/or fiber optic connections. In one embodiment, image processing program 116 and CADx module 118 can be a web service accessible via network 114 to a user of client device 104. In another embodiment, image processing program 116 and CADx module 118 may be operated directly by a user of server computer 102.

Client device 104 also includes user interface (UI) 120 and various programs (not shown). Examples of the various programs on client device 104 include: a web browser, an e-mail client, security software (e.g., a firewall program, a geo-locating program, an encryption program, etc.), an instant messaging (IM) application (app), and a communication (e.g., phone) application. In an example, a user of client device 104 can interact with user interface 120, such as a touch screen (e.g., display) that performs both input to a graphical user interface (GUI) and as an output device (e.g., a display) presenting a plurality of icons associated with software applications or images depicting the executing software application. Optionally, a software application (e.g., a web browser) can generate user interface 120 operating within the GUI of client device 104. User interface 120 accepts input from a plurality of input/output (I/O) devices including, but not limited to, a tactile sensor interface (e.g., a touch screen, a touchpad) referred to as a multi-touch display. An I/O device interfacing with user interface 120 may be connected to client device 104, which may operate utilizing wired (e.g., USB port) or wireless network communications (e.g., infrared, NFC, etc.).

Figure 2:
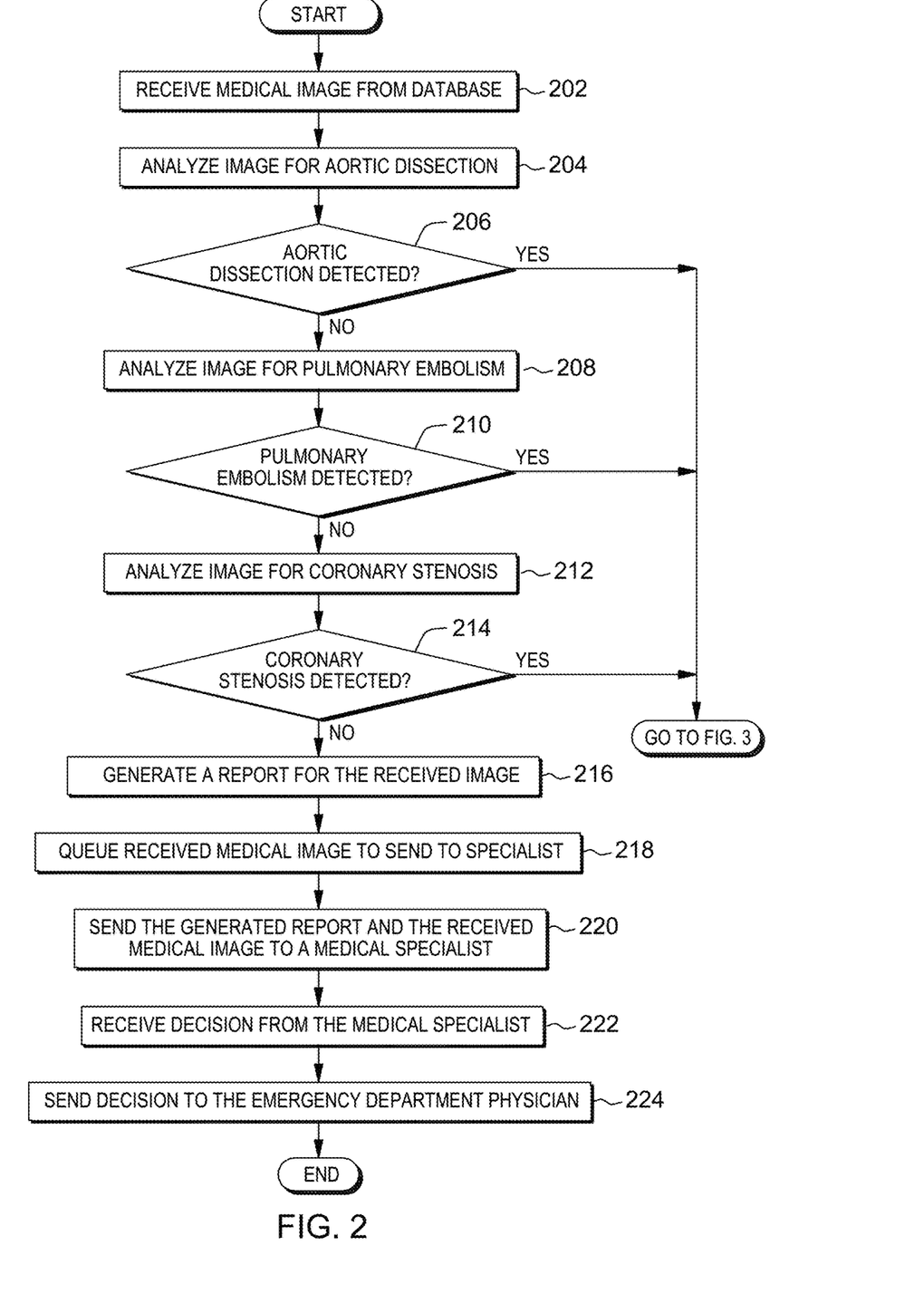
FIG. 2 is a flowchart depicting operational steps of an image processing program for detecting medical conditions, in accordance with an embodiment of the present invention.

FIG. 2 is a flowchart depicting operational steps of an image processing program for detecting medical conditions, in accordance with an embodiment of the present invention.

Image processing program 116 receives a medical image from a database (202). In this embodiment, image processing program 116 receives a medical image from a database (e.g., image database 108), where the medical image is a computed tomography (CT) scan of a patient's chest produced by an imaging device (i.e., CT Scan). The medical image that image processing program 116 receives can include additional sensitive information embedded in the metadata of the medical image file. The additional sensitive information can include patient's name, identification number, date of birth, age, gender, and list of known medical conditions of the patient. The medical image that image processing program 116 receives can also include non-sensitive information embedded in the metadata of the medical image file or directly viewable on the medical image. The non-sensitive information can include a date for when the medical image was produced, a location for where the medical image was produced (e.g., hospital name and department name), and an imaging device identification and model number which created the received image.

Image processing program 116 analyzes the medical image for aortic dissection (204). In this embodiment, the medical image is a volume CT, where the volume CT provides a three-dimensional view of a body part (e.g., chest) of a patient. Image processing program 116 can utilize atlas-based segmentation or other segmentation algorithms known in the art to identify the aorta and create two-dimensional views (i.e., slices) of the aorta, wherein the two-dimensional views are perpendicular to the aorta at a point along the aortic center line. In one example, the created two-dimensional image is at a first angle (e.g., 45-degrees) based on a plurality of slices of the received medical image at a second angle (e.g., 0-degrees). In an embodiment, the received medical image is a CT scan on an X-Axis (i.e., 0-degrees) but an aortic center line is at a 45-degree angle. Image processing program 116 can utilizes a plurality of slices of the medical image, to create the two-dimensional image at the appropriate angle (i.e., 45-degrees). Image processing program 116 analyzes each two-dimensional view for detection of a flap (i.e., indicator of dissection) or for detection of an irregular shape (i.e., indicator of dissection with thrombosis) based on a multiple historic images that include the aorta with the flap or the irregular shape. Image processing program 116 can utilizes a ridge enhancing filter for the detecting the flap and a circularity measure to detect the irregular shape. In an alternative embodiment, image processing program 116 utilizes a machine learning algorithm that can be trained to detect both the flap and the irregular shape of the aorta, where each image processed is utilized for future detections and comparisons. Upon detection of the flap or the irregular shape in a cross-section image of the aorta, image processing program 116 determines if aortic dissection is present.

Image processing program 116 determines whether aortic dissection is detected (decision 206). In the event, image processing program 116 determines aortic dissection is not detected ("no" block, decision 206), image processing program 116 analyzes the medical image for pulmonary embolism (208). In the event, image processing program 116 determines aortic dissection is detected ("yes" block, decision 206), image processing program 116 generates a synthetic image of the detected condition (302). It is to be noted, image processing program can determine whether aortic dissection, pulmonary embolism, and coronary stenosis is detected in a parallel process. Additionally, a detection of one condition (e.g., aortic dissection) is independent from a detection of another condition (e.g., coronary stenosis).

Image processing program 116 analyzes the medical image for pulmonary embolism (208). In this embodiment, image processing program 116 can utilize atlas-based segmentation or other segmentation algorithms known in the art to automatically compare signal intensity variations within the pulmonary blood vessel to a pre-determined range of signal intensity variations of non-enhanced blood or blood clots. Comparing the signal intensity variations allows for image processing program 116 to detect possible blood clots in the pulmonary blood vessels. In an alternative embodiment, image processing program 116 utilizes a machine learning algorithm that can be trained to detect true blood clots from a set of potential blood clots, where image processing program 116 can automatically detect a blood clot without comparing signal intensity variations of a blood clot and the pulmonary blood vessels.

Image processing program 116 determines whether pulmonary embolism is detected (decision 210). In the event, image processing program 116 determines pulmonary embolism is not detected ("no" block, decision 210), image processing program 116 analyzes the medical image for coronary stenosis (212). In the event, image processing program 116 determines pulmonary embolism is detected ("yes" block, decision 210), image processing program 116 generates a synthetic image of the detected condition (302).

Image processing program 116 analyzes the medical image for coronary stenosis (212). In this embodiment, image processing program 116 can utilize atlas-based segmentation or other segmentation algorithms known in the art to identify a centerline of each blood vessel and determine multiple diameters for each blood vessel along the identified centerline. Image processing program 116 can compare the multiple determined diameters to a diameter threshold. If one of the multiple determined diameters is below the diameter threshold, image processing program 116 determines coronary stenosis is present.

Image processing program 116 determines whether coronary stenosis is detected (decision 214). In the event, image processing program 116 determines coronary stenosis is not detected ("no" block, decision 214), image processing program generates a report for the received image (216). In the event, image processing program 116 determines coronary stenosis is detected ("yes" block, decision 214), image processing program 116 generates a synthetic image of the detected condition (302).

Image processing program 116 generates a report for the received image (216). In this embodiment, image processing program 116 generates a report for the received image, where the report includes information for the analysis performed on the received image for aortic dissection, pulmonary embolism, and coronary stenosis. Image processing program 116 can also generate a synthetic image even if a condition was not detected, to show the doctor (i.e., specialist) why there was a lack of detection. The type of synthetic images are discussed in further detail with regards to FIG. 3. For the image analysis performed for aortic dissection, image processing program 116 can include the created two-dimensional views of the aorta and an enhanced image of potential detections of a flap or irregular shape, where the potential detections of the flap or the irregular shape did not meet a threshold for aortic dissection. Image processing program 116 can also include one or more previously received images and previously created two-dimensional views that did not include aortic dissection, to which the received image and presently created two-dimensional views were compared. For the image analysis performed for pulmonary embolism, image processing program 116 can include the pre-determined known range of signal intensity variations of non-enhanced blood or blood clots to which the signal intensity within the pulmonary blood vessel in the received image were compared. Image processing program 116 can indicate in the report that the signal intensity within the pulmonary blood vessel in the received image was not with the pre-determined known range of signal intensity variations of non-enhanced blood or blood clots.

For the image analysis performed for coronary stenosis, image processing program 116 can include a generated imaged based on the received image, where the generated image indicates a centerline of each blood vessel and multiple diameter measurements of each blood vessel relative to the indicated centerline. For each diameter measurement, image processing program 116 can calculate a deviation from the diameter threshold and can highlight the diameter if the deviation is below a pre-determined value. The highlighted diameter in the generated image or in a listing of the multiple diameters, alerts a user (i.e., medical specialist) that the diameter is approaching the diameter threshold and to take preemptive action measures to prevent the diameter from reaching the diameter threshold.

Image processing program 116 queues the received medical image to send to a medical specialist (218). In this embodiment, image processing program 116 queues the received image based on a time and date for when image processing program 116 generated the report for the received image (216). The latest generated report is placed at the back of the queue, while the oldest generated report is located at the front of the queue. In another embodiment, image processing program 116 can queue the received medical image based on a determined priority for each of the received images. Image processing program 116 can utilize a number of identified preemptive action measures in each generated report to assign priority to each received image. The greater the number of identified preemptive action measures for the received image, the greater the priority image processing program 116 assigns the received image. The lower the number of identified preemptive action measures for the received image, the lower the priority image processing program 116 assigns the received image. Image processing program 116 can queue the received images based on the assigned priority and dynamically alter the queue with each received image. To ensure a received image is not queued for an extended period of time, image processing program 116 can base priority on a duration of time a received image and generated report is queued. Image processing program 116 can continuously process large quantities of received medical images and associated generated reports, while concurrently receiving additional medical images and associated generated reports. As result, image processing program 116 prevents oversight in the event a received medical image is not addressed in a timely manner by a specialist.

Image processing program 116 sends the generated report and the received medical image to the medical specialist (220). In this embodiment, image processing program 116 identifies a medical specialist and sends the generated report and the received medical image that is next in the queue of received medical images and associated generated reports. Image processing program 116 can identify a medical specialist based on availability and expertise at a given location (i.e., hospital) and send the generated report and received medical image to an electronic device associated with the medical specialist via electronic messaging. Image processing program 116 can also utilize an encrypted login method for accessing the generated report and received medical image to protect the privacy of the patient. Image processing program 116 can also include selectable options in the electronic message that includes the generated report and the received medical image. The selectable options can include confirming the non-detection of aortic dissection, pulmonary embolism, and coronary stenosis, forwarding to another medical specialist, requesting additional medical images, rejecting the non-detection, and selecting a condition of aortic dissection, pulmonary embolism, and/or coronary stenosis that is present in the received medical image.

Image processing program 116 receives a decision from the medical specialist (222). In one embodiment, image processing program 116 receives a decision from the medical specialist that confirms the non-detection of aortic dissection, pulmonary embolism, and coronary stenosis. Image processing program 116 can proceed to send the decision from the medical specialist that confirms the non-detection to the emergency department physician. In another embodiment, image processing program 116 receives a decision from the medical specialist that includes forwarding the received medical image and the generated report to another medical specialist, prior to sending the received decision to the emergency department physician. As a result, image processing program 116 reverts to 220 (not illustrated in FIG. 2) and sends the generated report and the received medical image to another medical specialist.

In another embodiment, image processing program 116 receives a decision from the medical specialist that includes requesting additional medical images. Image processing program 116 can send the request for additional medical images, prior to the medical specialist confirm the non-detection of aortic dissection, pulmonary embolism, and coronary stenosis. In yet another embodiment, image processing program 116 receives a decision from the medical specialist that includes rejecting the non-detection, where the rejection includes additional notes that the medical specialist provided or the selection of a condition of aortic dissection, pulmonary embolism, and/or coronary stenosis that is present in the received medical image. Additionally, image processing program 116 can flag the received medical image as a misdiagnosis and utilize the flagged received medical image for comparison in the machine learning algorithm when performing analysis on future medical images for aortic dissection, pulmonary embolism, and coronary stenosis.

Image processing program 116 sends the received decision to the emergency department physician (224). In this embodiment, image processing program 116 sends the received decision to the emergency department physician, where the medical specialist confirms the non-detection of aortic dissection, pulmonary embolism, and coronary stenosis. In another embodiment, image processing program 116 sends the received decision to the emergency department physician, where the medical specialist rejects the non-detection and includes additional notes that the medical specialist provided or the selection of a condition of aortic dissection, pulmonary embolism, and/or coronary stenosis that is present in the received medical image. In another embodiment, image processing program 116 sends the received decision to the emergency department physician, where the decision is from two medical specialists that includes confirmation of the non-detection of aortic dissection, pulmonary embolism, and coronary stenosis.

Figure 3:
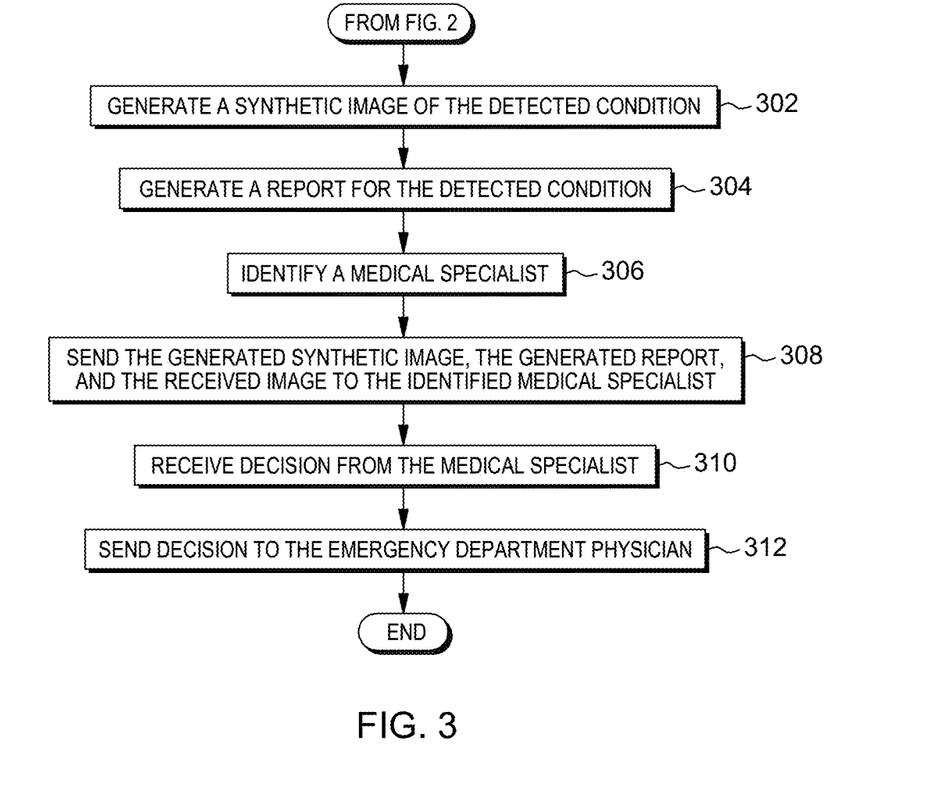
FIG. 3 is a flowchart operational steps of an image processing program for generating and sending synthetic images and medical reports to medical specialists, in accordance with an embodiment of the present invention.

FIG. 3 is a flowchart operational steps of an image processing program for generating and sending synthetic images and medical reports to medical specialists, in accordance with an embodiment of the present invention.

Image processing program 116 generates a synthetic image of the detected condition (302). In this embodiment, image processing program 116 generates a synthetic image of the detected condition based on the received medical image, where the detected condition is aortic dissection. The synthetic image highlights the true lumen and the false lumen indicating aortic dissection, where the true lumen (e.g., red) is highlighted in a manner distinctly different the false lumen (e.g., blue). In another embodiment, image processing program 116 generates a synthetic image of the detected condition based on the received medical image, where the detected condition is pulmonary embolism. Image processing program 116 can highlight each embolus in the pulmonary trunk, where each highlight covers an entire area of an embolus.

In another embodiment, image processing program 116 generates a synthetic image of the detected condition based on the received medical image, where the detected condition is coronary stenosis. In the generated image, image processing program 116 can highlight an area of the coronary vessel that is narrowing and include measured diameters along the length of coronary vessel to indicate the progression of the narrowing. Image processing program 116 can include a table of the measured diameters in a corner of the generated image, where measured diameters that fall below a predetermined diameter threshold are highlighted. Alternatively, image processing program 116 can incorporate an indicator, such as an arrow, directed at the area where narrowing of the coronary vessel is occurring. Image processing program 116 can generate a synthetic image of the aortic dissection, pulmonary embolism, and coronary stenosis that simplifies features in the surrounding area to draw attention to the detected condition. The simplification of features in the area can include removing image noise, blurring out (i.e., out of focus) items, and/or darkening the items that were not part of the analysis in 204, 208, and 212.

Image processing program 116 generates a report for the detected condition (304). In this embodiment, image processing program 116 generates a report for the received medical image, where the report includes information for the analysis performed on the received image for aortic dissection, pulmonary embolism, and coronary stenosis. For the image analysis performed for aortic dissection, image processing program 116 can include the created two-dimensional views of the aorta and an enhanced image of potential detections of a flap or irregular shape, where the potential detections of the flap or the irregular shape met a threshold for aortic dissection. Image processing program 116 can also include one or more previously received images and previously created two-dimensional views that include aortic dissection, to which the received image and presently created two-dimensional views were compared.

For the image analysis performed for pulmonary embolism, image processing program 116 can include the predetermined known range of signal intensity variations of non-enhanced blood or blood clots to which the signal intensity within the pulmonary blood vessel in the received image were compared. Image processing program 116 can indicate in the report that the signal intensity within the pulmonary blood vessel in the received image was within the pre-determined range of signal intensity variations of non-enhanced blood or blood clots.

For the image analysis performed for coronary stenosis, image processing program 116 can include each diameter measurement along the coronary vessel, highlighting the diameters that fall below the diameter threshold. Image processing program 116 can plot the diameters on a graph based on a position along the length of the coronary vessel, to illustrate the progression of the narrowing of the coronary vessel.

Image processing program 116 identifies a medical specialist (306). In this embodiment, image processing program 116 identifies a medical specialist based on availability and expertise at a given location (i.e., hospital). Image processing program 116 can identify a medical specialist that is on-call, with expertise in identifying the condition detected (e.g., aortic dissection). Image processing program 116 can select a medical specialist based on a set of rules, where the set of rules can assign rank to each medical specialist based on years of expertise, areas of expertise, location, and availability (e.g., shift hours and vacation). In another embodiment, image processing program 116 can identify two medical specialists on-call but located remotely (i.e., off-site), if image processing program 116 determines that a medical specialist on-site and on-call is unavailable to review the condition detected in the received medical image.

Image processing program 116 sends the generated synthetic image, the generated report, and the received image to the identified medical specialist (308). In this embodiment, image processing program 116 sends the generated synthetic image, the generated report, and received medical image to an electronic device associated with the identified medical specialist via electronic messaging. Image processing program 116 can utilize an encrypted login method for accessing the generated synthetic image, generated report, and received medical image to protect the privacy of the patient. Image processing program 116 allows for selectable options in the electronic message that includes the generated synthetic image, generated report, and received medical image. The selectable options can include confirming the detection of aortic dissection, pulmonary embolism, and/or coronary stenosis, forwarding to another medical specialist, requesting additional medical images, and rejecting the detection.

Image processing program 116 receives a decision from the medical specialist (310). In one embodiment, image processing program 116 receives a decision from the medical specialist that confirms the detection of aortic dissection, pulmonary embolism, and/or coronary stenosis. Image processing program 116 can proceed to send the decision from the medical specialist that confirms the detection to the emergency department physician. In another embodiment, image processing program 116 receives a decision from the medical specialist that includes forwarding the received medical image and the generated report to another medical specialist, prior to sending the received decision to the emergency department physician. As a result, image processing program 116 reverts to 308 (not illustrated in FIG. 3) and sends the generated synthetic image, the generated report, and the received medical image to another medical specialist.

In another embodiment, image processing program 116 receives a decision from the medical specialist that includes requesting additional medical images. Image processing program 116 can send the request for additional medical images, prior to the medical specialist confirm the detection of aortic dissection, pulmonary embolism, and/or coronary stenosis. In yet another embodiment, image processing program 116 receives a decision from the medical specialist that includes rejecting the detection, where the rejection includes additional notes that the medical specialist provided. Additionally, image processing program 116 can flag the received medical image as a misdiagnosis and utilize the flagged received medical image for comparison in the machine learning algorithm when performing analysis on future medical images for aortic dissection, pulmonary embolism, and coronary stenosis.

Image processing program 116 sends the received decision to the emergency department physician (312). In this embodiment, image processing program 116 sends the received decision to the emergency department physician, where the medical specialist confirms the detection of aortic dissection, pulmonary embolism, and/or coronary stenosis. In another embodiment, image processing program 116 sends the received decision to the emergency department physician, where the medical specialist rejects the detection and includes additional notes that the medical specialist. In another embodiment, image processing program 116 sends the received decision to the emergency department physician, where the decision is from two medical specialists that includes confirmation of the detection of aortic dissection, pulmonary embolism, and/or coronary stenosis. Subsequent to image processing program 116 sending the received decision to the emergency department physician, triaging of the patient associated with the received image may begin.

Figure 4:
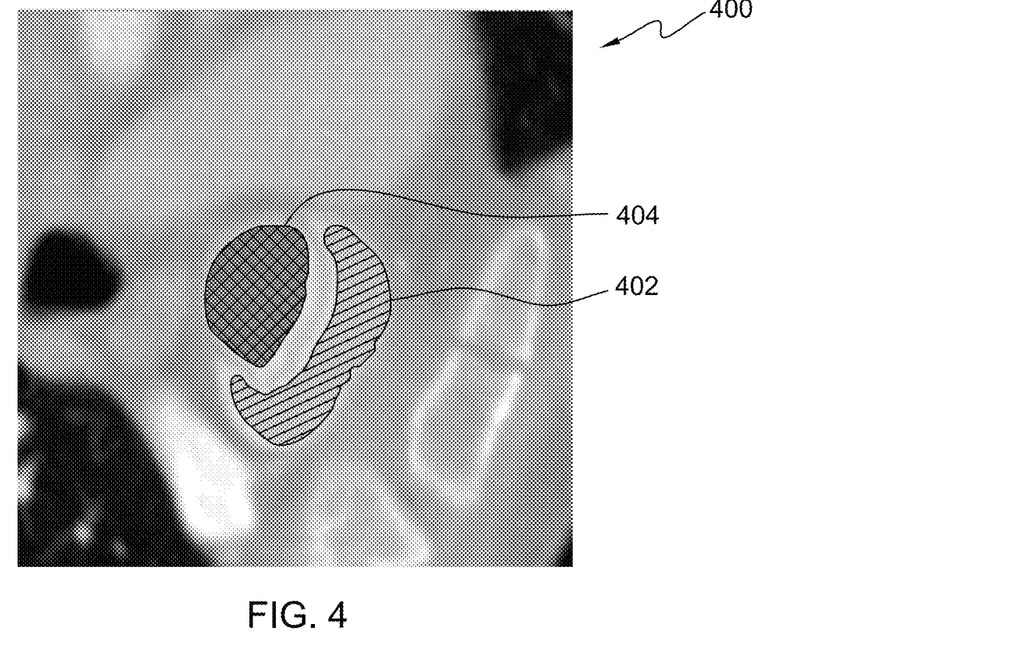
FIG. 4 is an example image of a synthetic image of an aortic dissection generated by image processing program, in accordance with an embodiment of the present invention.

FIG. 4 is an example image of a synthetic image of an aortic dissection generated by image processing program, in accordance with an embodiment of the present invention. In this example, image processing program 116 generates synthetic image 400 based on a received medical image of a patient's chest, where synthetic image 400 is a two-dimensional view of an aorta perpendicular to the aortic center line. The synthetic image highlights true lumen 402 and false lumen 404 indicating aortic dissection, where image processing program 116 highlights true lumen 402 in a manner distinctly different false lumen 404.

Figure 5:
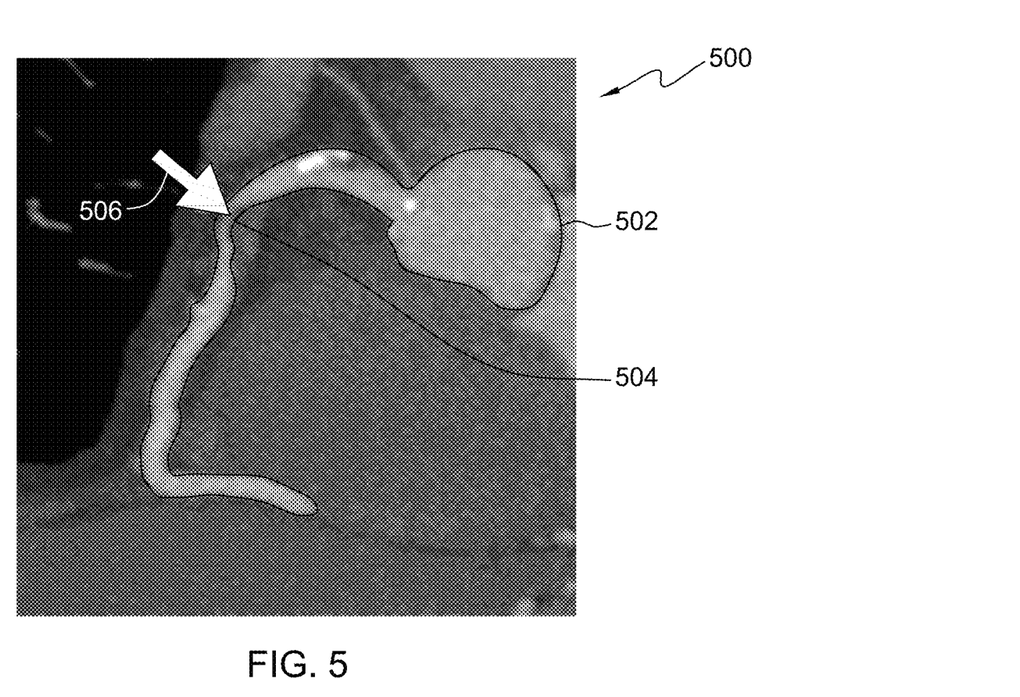
FIG. 5 is an example image of a synthetic image of a coronary stenosis generated by image processing program, in accordance with an embodiment of the present invention.

FIG. 5 is an example image of a synthetic image of a coronary stenosis generated by image processing program, in accordance with an embodiment of the present invention. In this example, image processing program 116 generates synthetic image 500 based on a received medical image of coronary vessel 502. Coronary vessel 502 has various diameters along the length of the vessel, where section 504 is a portion of coronary vessel 502 for which image processing program 116 determines that the diameter of the portion falls below a diameter threshold and coronary stenosis is detected. Arrow 506 indicates the location of coronary stenosis in section 504.

Figure 6:
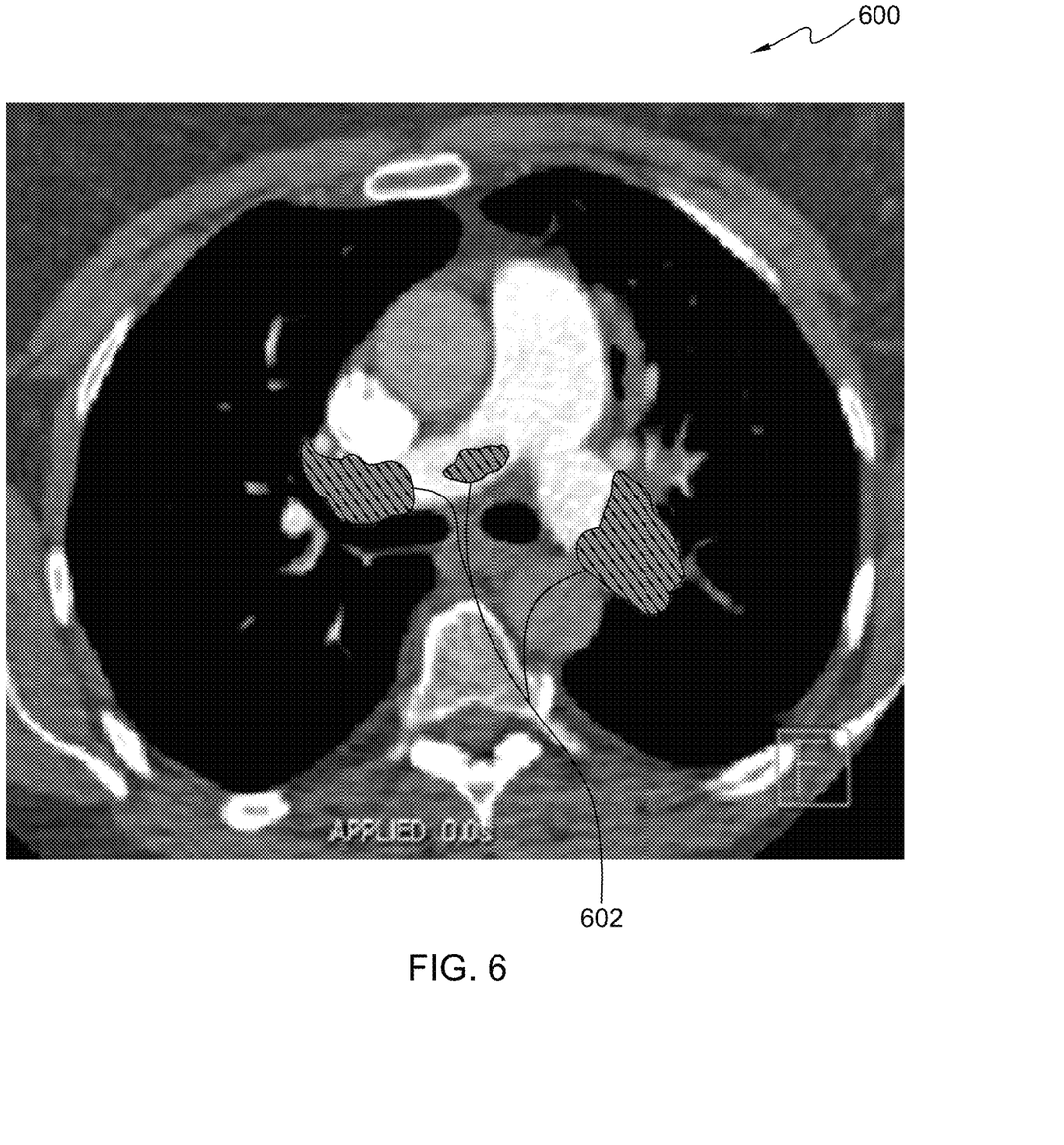
FIG. 6 is an example image of a synthetic image of a pulmonary embolism generated by image processing program, in accordance with an embodiment of the present invention.

FIG. 6 is an example image of a synthetic image of a pulmonary embolism generated by image processing program, in accordance with an embodiment of the present invention. In this example, image processing program 116 generates synthetic image 600 based on a received medical image of a pulmonary blood vessel. The pulmonary blood vessel includes blood clots 602, where image processing program 116 highlights blood clots 602 in the generated synthetic image 600. Due to the surrounding signal intensity variations and image noise, highlighting blood clots 602 allows for clear distinctions between items in the surrounding area.

Figure 7:
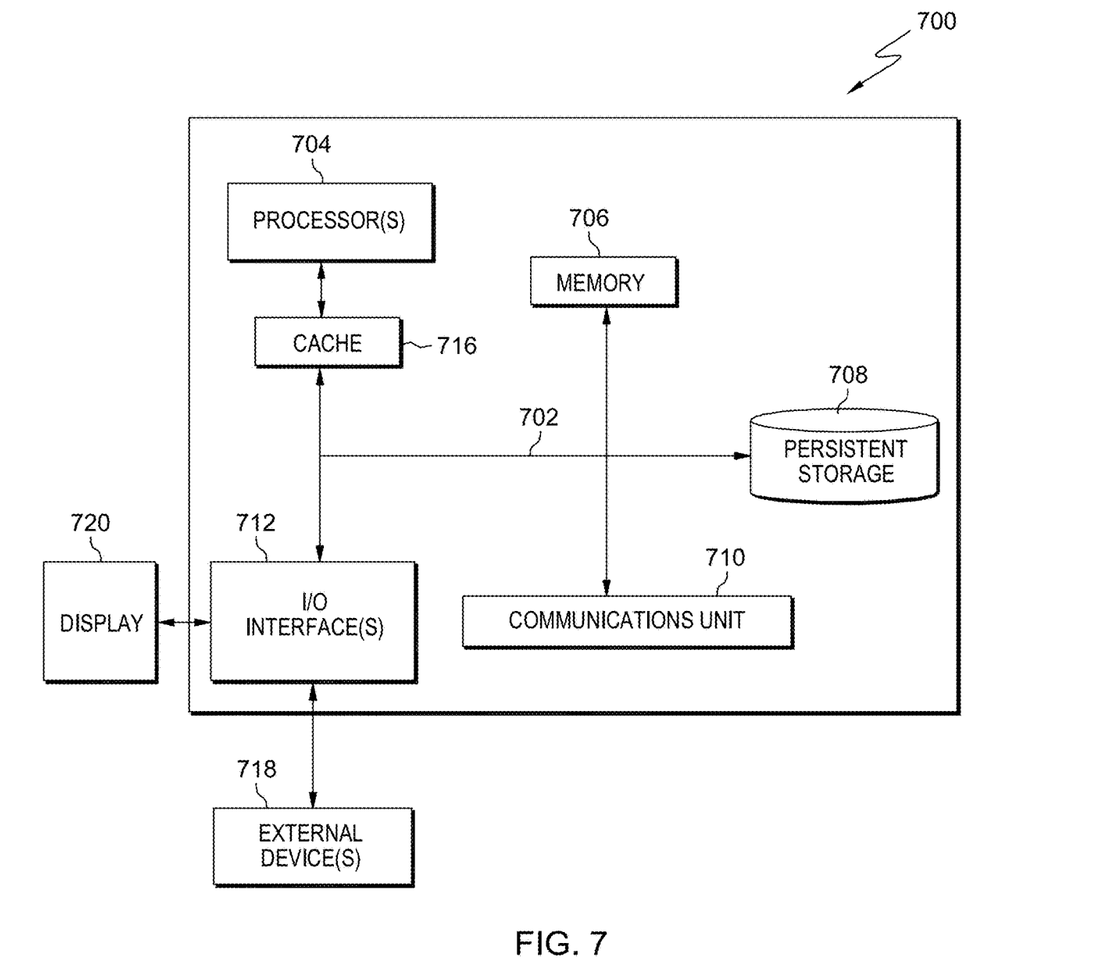
FIG. 7 is a block diagram of components of a computer system, such as the server computer of FIG. 1, in accordance with an embodiment of the present invention.

FIG. 7 depicts computer system 600, where server computer 102 is an example of a system that includes image processing program 116 and computer aided diagnosis module module 118. The computer system includes processors 604, cache 616, memory 606, persistent storage 608, communications unit 610, input/output (I/O) interface(s) 612 and communications fabric 602. Communications fabric 602 provides communications between cache 616, memory 606, persistent storage 608, communications unit 610, and input/output (I/O) interface(s) 612. Communications fabric 602 can be implemented with any architecture designed for passing data and/or control information between processors (such as microprocessors, communications and network processors, etc.), system memory, peripheral devices, and any other hardware components within a system. For example, communications fabric 602 can be implemented with one or more buses or a crossbar switch.

Memory 606 and persistent storage 608 are computer readable storage media. In this embodiment, memory 602 includes random access memory (RAM). In general, memory 606 can include any suitable volatile or non-volatile computer readable storage media. Cache 616 is a fast memory that enhances the performance of processors 604 by holding recently accessed data, and data near recently accessed data, from memory 606.

Program instructions and data used to practice embodiments of the present invention may be stored in persistent storage 608 and in memory 606 for execution by one or more of the respective processors 604 via cache 616. In an embodiment, persistent storage 608 includes a magnetic hard disk drive. Alternatively, or in addition to a magnetic hard disk drive, persistent storage 608 can include a solid state hard drive, a semiconductor storage device, read-only memory (ROM), erasable programmable read-only memory (EPROM), flash memory, or any other computer readable storage media that is capable of storing program instructions or digital information.

The media used by persistent storage 608 may also be removable. For example, a removable hard drive may be used for persistent storage 608. Other examples include optical and magnetic disks, thumb drives, and smart cards that are inserted into a drive for transfer onto another computer readable storage medium that is also part of persistent storage 608.

Communications unit 610, in these examples, provides for communications with other data processing systems or devices. In these examples, communications unit 610 includes one or more network interface cards. Communications unit 610 may provide communications through the use of either or both physical and wireless communications links. Program instructions and data used to practice embodiments of the present invention may be downloaded to persistent storage 608 through communications unit 610.

I/O interface(s) 612 allows for input and output of data with other devices that may be connected to each computer system. For example, I/O interface 606 may provide a connection to external devices 618 such as a keyboard, keypad, a touch screen, and/or some other suitable input device. External devices 618 can also include portable computer readable storage media such as, for example, thumb drives, portable optical or magnetic disks, and memory cards. Software and data used to practice embodiments of the present invention can be stored on such portable computer readable storage media and can be loaded onto persistent storage 608 via I/O interface(s) 612. I/O interface(s) 612 also connect to display 620.

Display 620 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method comprising:
   creating, by one or more processors, a two-dimensional image of the medical image to detect a medical condition that includes aortic dissection, wherein the two-dimensional view is a cross-sectional view of an aorta perpendicular to a point along the aorta center line, wherein the two-dimensional image is created at a first angle from a plurality of slices of the medical image at a second angle;

determining, by one or more processors, whether a flap present based on a plurality of historic images, wherein the flap in the aorta indicates aortic dissection;

responsive to determining the medical image includes a first medical condition, generating, by one or more processors, a first report that includes information on a detection of the first medical condition;

identifying, by one or more processors, a medical specialist based on availability and medical expertise;

sending, by one or more processors, to a first electronic device associated with the identified medical specialist, the medical image and the first report to receive a decision on the detection of the first medical condition from the identified medical specialist; and responsive to receiving the decision from the medical specialist, sending, by one or more processors, to a second electronic device, the decision, the medical image, and the first report.

2. The method of claim 1, further comprising:

generating, by one or more processors, a synthetic image based on the medical image highlighting the first medical condition in the medical image.

3. The method of claim 2, further comprises:

sending, by one or more processors, to the first electronic device associated with the identified medical specialist, the synthetic image.

4. The method of claim of 1, wherein identifying a medical specialist is based on availability and location.

* * * * *